(12) United States Patent  (10) Patent No.: US 7,355,706 B2
Girvin et al.  (45) Date of Patent: Apr. 8, 2008

(54) PARTICLE DETECTION SYSTEM IMPLEMENTED WITH AN IMMERSED OPTICAL SYSTEM

(75) Inventors: Kenneth L. Girvin, Grants Pass, OR (US); Richard K. DeFreez, Azalea, OR (US); James Brady, Ashland, OR (US)

(73) Assignee: Hach Ultra Analytics, Inc., Grants Pass, OR (US)

( * ) Notice: Subject to any disclaimer, the term of this patent is extended or adjusted under 35 U.S.C. 154(b) by 196 days.

(21) Appl. No.: 11/241,216

(22) Filed: Sep. 30, 2005

(65) Prior Publication Data

US 2006/0132770 A1 Jun. 22, 2006

Related U.S. Application Data

(63) Continuation-in-part of application No. 10/927,671, filed on Aug. 27, 2004, now abandoned, which is a continuation of application No. 10/407,650, filed on Apr. 4, 2003, now Pat. No. 6,784,990.

(51) Int. Cl.
*G01N 21/00* (2006.01)
*G01N 15/00* (2006.01)

(52) U.S. Cl. ...................... 356/338; 356/336
(58) Field of Classification Search ............... 356/336, 356/338
See application file for complete search history.

(56) References Cited

U.S. PATENT DOCUMENTS

| 4,422,761 A | 12/1983 | Frommer | 356/338 |
|---|---|---|---|
| 4,761,381 A * | 8/1988 | Blatt et al. | 436/165 |
| 4,984,889 A | 1/1991 | Sommer | 356/336 |
| 5,467,189 A | 11/1995 | Kreikebaum et al. | 356/336 |
| 5,726,753 A | 3/1998 | Sandberg | 356/338 |
| 5,731,875 A | 3/1998 | Chandler et al. | 356/336 |
| 5,767,967 A | 6/1998 | Yufa | 356/336 |
| 5,805,281 A | 9/1998 | Knowlton et al. | 356/336 |
| 5,815,264 A | 9/1998 | Reed et al. | 356/343 |
| 5,824,269 A * | 10/1998 | Kosaka et al. | 422/73 |
| 5,999,250 A | 12/1999 | Hairston et al. | 356/336 |
| 6,016,194 A | 1/2000 | Girvin et al. | 356/337 |
| 6,104,491 A * | 8/2000 | Trainer | 356/336 |
| 6,137,572 A | 10/2000 | DeFreez et al. | 356/336 |
| 2001/0035954 A1 | 11/2001 | Rahn et al. | 356/336 |

* cited by examiner

*Primary Examiner*—Tarifur Chowdhury
*Assistant Examiner*—Tara S Pajoohi
(74) *Attorney, Agent, or Firm*—Stoel Rives LLP (57) ABSTRACT

Fluid-based particle detection exhibits improved light collection and image quality from a light collection system that uses immersed optics on a flow-through cell for collecting and detecting scattered light from particles carried by the fluid. The flow-through cell includes first and second body sections that are coupled to form a unitary article and have opposed interior surface portions configured to form opposed walls of a flow channel through which the fluid flows. First and second optical elements are associated with the respective first and second body sections. In certain embodiments, at least one of the first and second optical elements is an integral part of its associated body section. A lens element constructed as an integral part of the unitary flow-through cell eliminates additional interfaces or bonding joints that cause scattering and absorption of light.

18 Claims, 9 Drawing Sheets

PARTICLE DETECTION SYSTEM IMPLEMENTED WITH AN IMMERSED OPTICAL SYSTEM

RELATED APPLICATIONS

This application is a continuation-in-part of U.S. patent application Ser. No. 10/927,671, filed Aug. 27, 2004, for PARTICLE DETECTION SYSTEM, abandoned, which is a continuation of U.S. patent application Ser. No. 10/407,650, filed Apr. 4, 2003, now U.S. Pat. No. 6,784,990, for PARTICLE DETECTION SYSTEM IMPLEMENTED WITH A MIRRORED OPTICAL SYSTEM.

TECHNICAL FIELD

The present invention relates to optical particle detection and, in particular, to a particle detection system with increased sensitivity in the detection of submicron-diameter particles.

BACKGROUND INFORMATION

Contamination control, including particle monitoring, plays a critical role in the manufacturing processes of several industries. These industries require clean rooms or clean zones with active air filtration and require the supply of clean raw materials such as process gases, deionized water, chemicals, and substrates. In the pharmaceutical industry, the U.S. Food and Drug Administration requires particle monitoring because of the correlation between detected particles in an aseptic environment and viable and non-viable particles that contaminate the product being produced. Semiconductor fabrication companies require particle monitoring as an active part of quality control. As integrated circuits become more compact, line widths decrease, thereby reducing the size of particles that can cause quality problems. Accordingly, it is important to detect and accurately measure submicron-diameter particles of ever-decreasing sizes and numbers for each volumetric unit.

To perform particle monitoring, currently available commercial submicron-diameter particle detection systems use optical detection techniques to determine the presence, size, and number of particles in a volumetric unit. This technology is based on optical scattering of a light beam and detection of the optical signal after it has been scattered by a sample particle. The standard particle detection approach, which was developed during the late 1980s, entails intersecting, in a region referred to as a "view volume," a light beam and a fluid stream containing sample particles. Light scattered by a particle in the view volume is collected with optics and focused onto a detection system that includes one or more detector elements. The detection system includes a light detector that detects the incidence of light and generates a pulse output signal, the magnitude of which depends on the intensity of the scattered light. The magnitude of the pulse output signal is compared to a predetermined pulse output signal threshold that is typically slightly above the average noise of the system. If the pulse output signal is less than the threshold, the signal is ignored. If the pulse output signal is greater than the threshold, the signal is processed by a computer that measures the voltage of the pulse output signal and determines particle size therefrom. Consequently, the ability of a particle detection system to detect small particles depends on its ability to distinguish between noise and pulse output signals generated from light scattered by submicron-diameter sample particles.

What is needed, therefore, is a particle detection system having high sensitivity in detecting submicron-diameter particles.

SUMMARY OF THE INVENTION

Preferred embodiments of the invention improve light collection and image quality from a collection system of a fluid particle detection system by using immersed optics on a flow-through cell for collecting and detecting scattered light from particles. The particle detection system is capable of optically detecting particles in a fluid stream and includes a flow chamber within which a light beam propagating along a light propagation path and a fluid stream containing sample particles transversely intersect to form a view volume. The incidence of a sample particle with the light beam causes portions of the light beam to scatter from the view volume in the form of scattered light components. At least one scattered light component exits the view volume, is collected and focused by a light collection lens system, and is incident on a photodetector. The photodetector detects the incidence of the scattered light component and generates a pulse output signal correlating to a predetermined parameter (e.g., size) of the scattered light component.

The view volume of the particle detection system is located within a flow-through cell that includes first and second body sections that are coupled to form a unitary article. The first and second body sections have opposed interior surface portions that are configured to form opposed walls of a flow channel through which the fluid stream flows. First and second optical elements are associated with the respective first and second body sections. In certain embodiments, at least one of the first and second optical elements is an integral part of its associated body section. A lens element constructed as an integral part of the unitary flow-through cell, when compared to a lens attached to a flat cell wall, eliminates additional interfaces or bonding joints that cause scattering and absorption of light. The unitary flow-through cell is sized for insertion into the particle detection system in an orientation that positions the first and second optical elements along a light collection lens system axis.

In certain embodiments of the particle detection system, the flow-through cell includes a pair of spacers positioned between and coupled to the first and second body sections. The spacers are spaced apart from each other to define opposed interior surface portions that form the opposed walls of the flow channel. The spacers are formed of optically transparent material such that they function as ingress and egress windows of the view volume for the light beam. The first and second body sections and the pair of spacers may be fused into an integral structure such that the pair of spacers define surface interfaces between the spacers and the first and second body sections.

In certain embodiments of the particle detection system, one of the optical elements is a transparent optical element, lens, or mirror, and the other optical element is a lens. The presence of a lens in the flow-through cell increases the numerical aperture of the light collection lens system. Increasing the numerical aperture increases the collection angle and results in a corresponding increase in amount of light collected by the light collection lens system. An increase in the amount of light collected results in an increase in the magnitude of the pulse output signal generated by the detector.

Increasing the magnitude of the pulse output signal for a given particle size allows for detection of a smaller size particle at a given threshold. For a sensor that is not background light noise limited (i.e., the noise is dominated by detector and associated electronic noise), collecting more light will increase the magnitude of the output signal without increasing the noise. The threshold remains the same, but the signals that cross it correspond to smaller particles. Moreover, for a given particle detection size, increasing the magnitude of the signal allows for increasing the threshold farther away from the noise and thereby reduces false counting resulting from randomly occurring noise. Consequently, the pulse output signal threshold for a given false count rate may be increased, and the particle detection system can maintain the desired overall false count rate, since most noise is random and of insufficient magnitude to generate a pulse output signal that has a magnitude greater than the predetermined threshold.

Additional aspects and advantages will be apparent from the following detailed description of preferred embodiments, which proceeds with reference to the accompanying drawings.

DETAILED DESCRIPTION OF PREFERRED EMBODIMENTS

Figure 1:
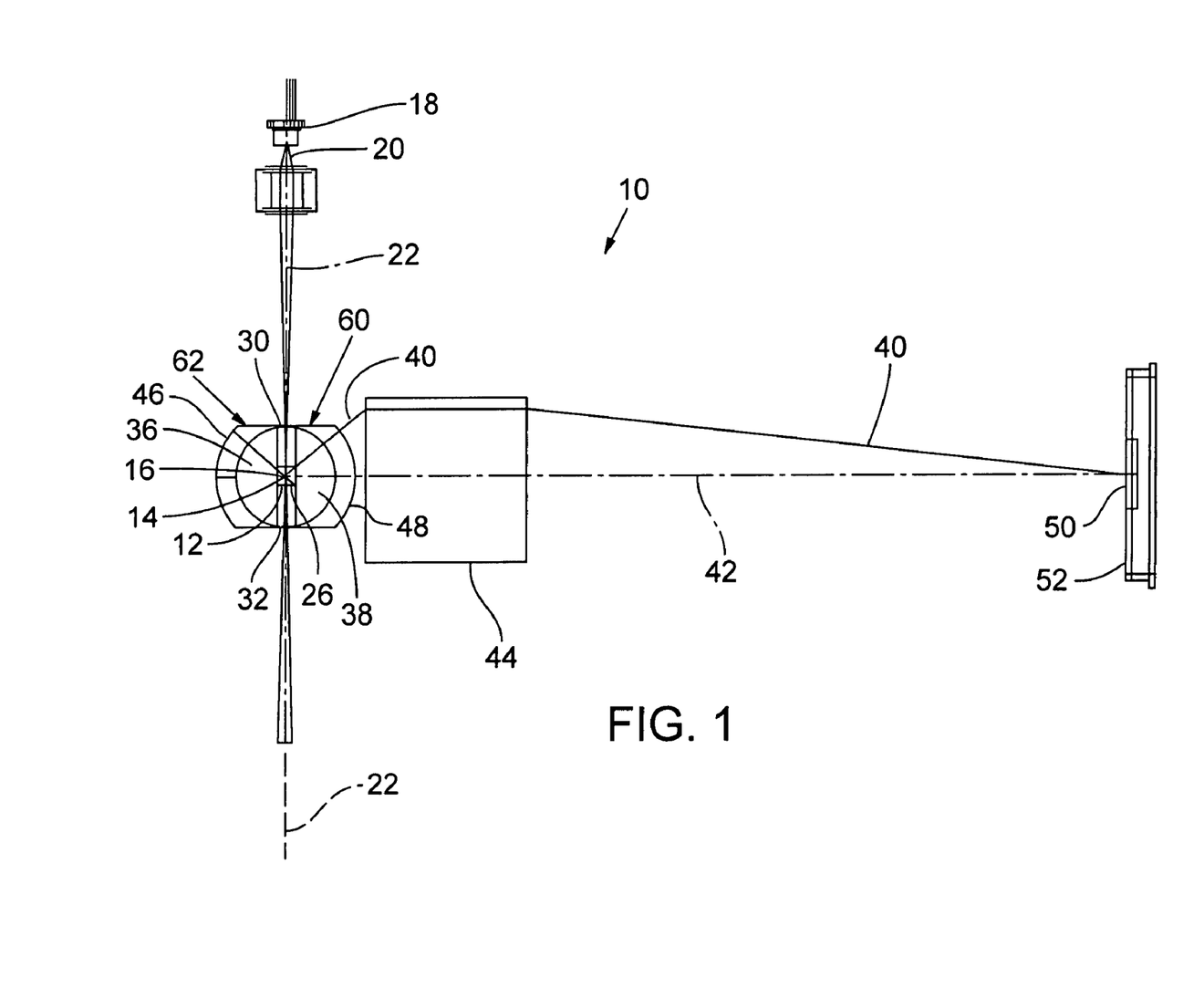
FIG. 1 is a plan view of an exemplary particle detection system implemented with an immersed optical system.

FIG. 1 is useful in explaining the configuration of an exemplary particle detection system 10. Particle detection system 10 includes a flow chamber 12 (extending out of the plane of FIG. 1) through which a particle-carrying sample fluid stream 14, such as gas (e.g., air) or liquid (e.g., water), flows in a flow direction 16 (out of the plane of FIG. 1). Particle detection system 10 also includes a light source 18 emitting a light beam 20 that propagates in a direction along an optical axis 22. Light source 18 is preferably a diode laser that is robust, efficient, and compact. Exemplary preferred light sources are gas, dye, and solid-state lasers.

Fluid stream 14 and light beam 20 intersect within the effective center of flow chamber 12 in a region called a view volume 26. View volume 26 is located within a unitary flow-through cell 28 that includes first and second spaced-apart, opposed optically transparent windows 30 and 32 through which light beam 20 propagates into and out of view volume 26. Unitary flow-through cell 28 also includes an optical element 36 that is spaced apart from and positioned in opposition to a lens 38 that collects a scattered light component 40 exiting view volume 26 along a collection system axis 42. Optical element 36 and lens 38 are positioned on opposite sides of fluid stream 14. Optically transparent windows 30 and 32 are preferably formed of an optically polished, transparent material, such as fused silica.

Optical element 36 is preferably a transparent lens or mirror made of glass, crystal, or plastic material. Scattered light component 40 can pass through optical element 36 or be reflected off of optical element 36 having a curved outer surface 46 coated with a high-reflectance coating material. Lens 38 is positioned between view volume 26 and a light collection lens system 44. Lens 38 is preferably a transparent, convex lens of elliptical, aspherical, or spherical shape. An outer surface 48 of lens 38 is preferably coated with an anti-reflective coating material. In a preferred embodiment, optical element 36 and lens 38 are of sufficient size that their interfaces with optically transparent windows 30 and 32 are not within the field of view of light collection lens system 44.

Light collection lens system 44 is positioned adjacent to unitary flow-through cell 28 and along collection system axis 42. Exemplary light collection lens systems are commonly known to those with skill in the art; however, a refractive light collection lens system is preferred. Light collection lens system 44 collects and images scattered light component 40 onto a light-receiving surface 50 of a photodetector element 52. Photodetector element 52 is positioned so that its light-receiving surface 50 is substantially perpendicular to collection system axis 42. Collection system axis 42 is orthogonal to optical axis 22 along which beam 20 propagates. Collecting light for viewing orthogonal to beam 20 facilitates light stop implementation in system 10 to significantly reduce detected stray light from the interfaces of optically transparent windows 30 and 32.

Photodetector element 52 generates a pulse output signal having a magnitude corresponding to the intensity of scattered light component 40, which is dependent on the size of the particle to which it corresponds. Signal processing takes place downstream of photodetector element 52 and converts the pulse output signal into a voltage that can be measured. Because particle size directly relates to light amplitude, which directly relates to pulse output signal amplitude, which directly relates to voltage magnitude, the size of a particle may be determined by measuring the voltage corresponding to each pulse output signal. The signal is preferably amplified before reaching the preamplifier stage, where inherent electronic noise is added to the signal. Because the signal has already been amplified, the proportional amount of electronic noise added at the preamplifier stage is smaller than what it would have been had the signal not been amplified before reaching the preamplifier stage.

Figure 2:
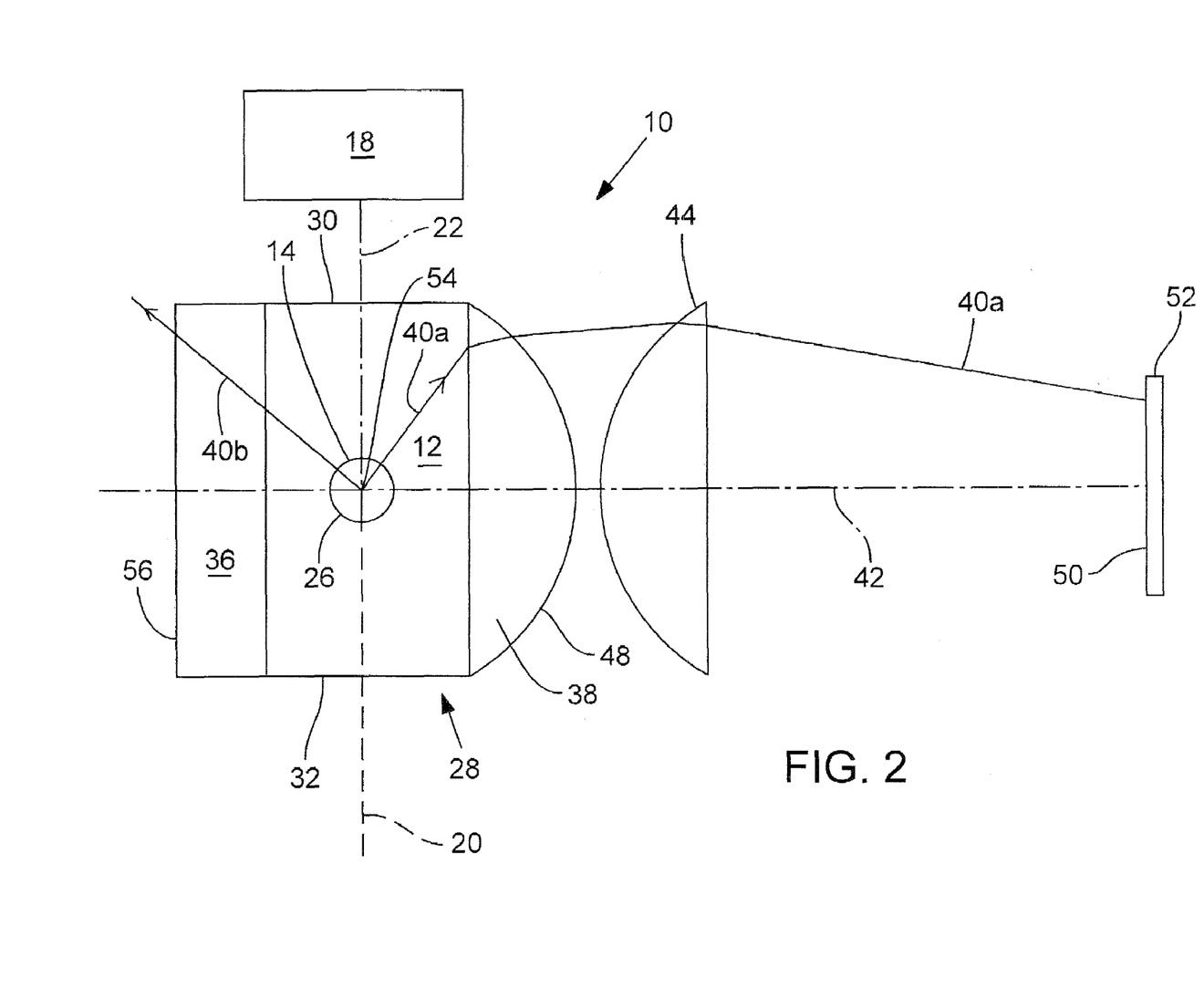
FIG. 2 is an enlarged, simplified plan view of an exemplary modified implementation of the particle detection system of FIG. 1.

FIG. 2 is useful in explaining the path of light beam 20 and scattered light components 40a and 40b as they progress through particle detection system 10 of FIG. 1. The width of laser beam 20 is the same as or is smaller than the width of optically transparent window 30. Laser beam 20 is of the same width when it is desired to illuminate flow chamber 12 in its entirety to achieve particle scattering, and laser beam 20 is focused to a smaller width to increase intensity and thereby enable detection of smaller particles. Typically, the widths of window 30 and beam 20 are the same. Following its incidence on a particle 54 present in view volume 26, light beam 20 exits view volume 26 as scattered light components 40a and 40b, which initially propagate in generally opposite directions. As shown in FIG. 2, a scattered light component 40a exits view volume 26 in a direction toward light collection lens system 44, and a scattered light component 40b exits view volume 26 in a direction toward optical element 36. (FIG. 2 shows optical element 36 having a flat outer surface 56, instead of curved outer surface 46 shown in FIG. 1.) In the exemplary embodiment shown in FIG. 2, scattered light component 40b passes through optical element 36 and exits particle detection system 10. Scattered light component 40a exits view volume 26, is incident on lens 38, and passes through light collection lens system 44, which focuses scattered light component 40a onto light-receiving surface 50 of photodetector element 52.

Figure 3A:
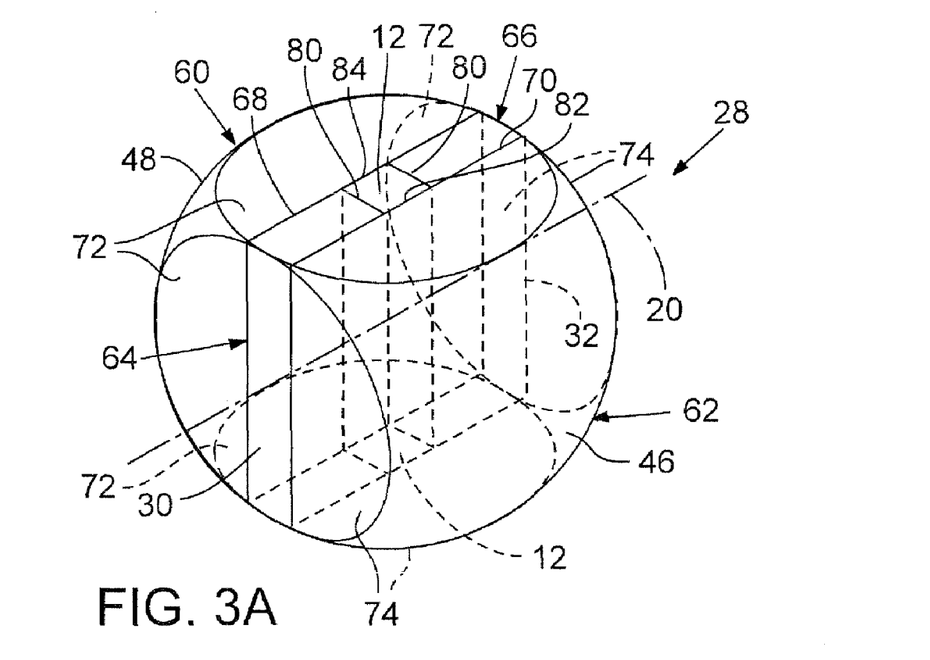
FIG. 3A is an isometric view of an exemplary unitary flow-through cell.
Figure 3B:
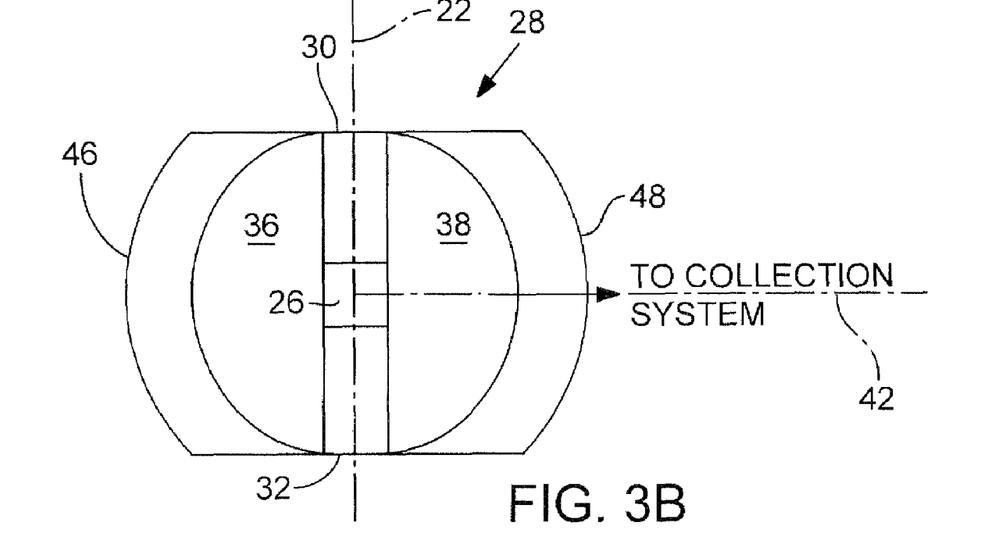
FIGS. 3B and 3C are, respectively, simplified plan and side elevation views of the exemplary unitary flow-through cell of FIG. 3A.
Figure 3C:
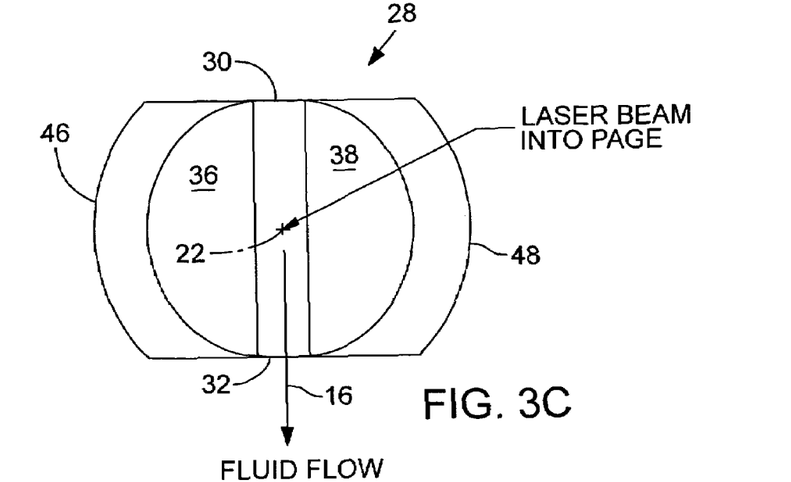

FIGS. 3A, 3B, and 3C are respective isometric, plan, and side elevation views of a preferred unitary flow-through cell 28. Flow-through cell 28 is in the form of two truncated hemispherical solid glass body sections 60 and 62 separated by spaced-apart rectangular spacers 64 and 66. All four components are assembled preferably by fusion at high temperatures to form fluid-tight seals between adhesive material-free adjacent component interfaces and thereby form a unitary article. If fitted together without spacers 64 and 66, body sections 60 and 62 would resemble two halves of a sphere that is truncated to have two sets of two opposed planar exterior surface regions of circular shape in which the sets are orthogonally aligned to each other. Body sections 60 and 62 have respective rectangular flat major surfaces 68 and 70. Flat major surfaces 68 and 70 are bordered by four respective semicircular flat surfaces 72 and 74, each of which corresponding to one-half of a planar exterior surface region of circular shape. When flow-through cell 28 is assembled, body sections 60 and 62 are spaced-apart by rectangular spacers 64 and 66 positioned between flat major surfaces 72 and 74 to form flow chamber 12 through which sample fluid stream 14 flows. Flow chamber 12 has a rectangular cross-sectional shape defined by opposed interior surface portions 80 of spacers 64 and 66 and opposed interior surface portions 82 and 84 of, respectively, optical element 36 and lens 38. Optical element 36 and lens 38 are "immersed" in that fluid flows in direct contact against their respective interior surface portions 82 and 84. Optically transparent windows 30 and 32 are formed by the larger area side surfaces of the respective spacers 64 and 66. Lens 38 and optical element 36 form portions of the respective body sections 60 and 62. View volume 26 lies between interior surface portions 80 of optically transparent windows 30 and 32 and between interior surface portions 82 and 84 of, respectively, optical element 36 and lens 38. The outer surfaces of optically transparent windows 30 and 32 are preferably coated with an anti-reflective coating.

Figure 4A:
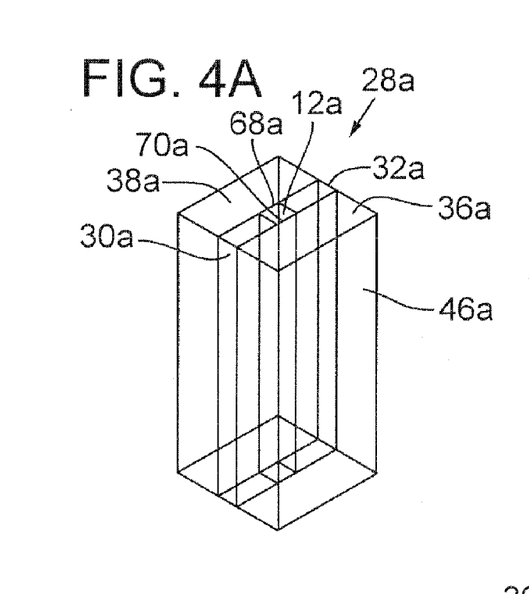
FIGS. 4A, 4B, and 4C are, respectively, isometric, plan, and side elevation views of an alternative exemplary unitary flow-through cell.
Figure 4B:
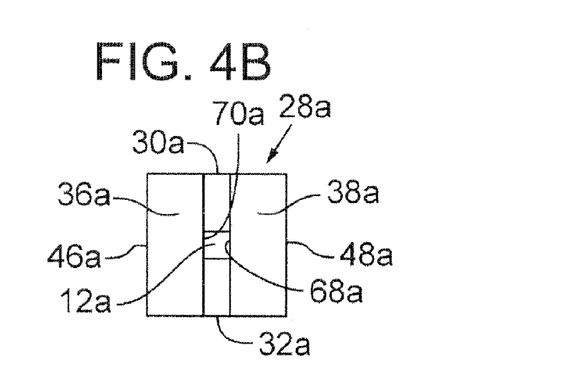
Figure 4C:
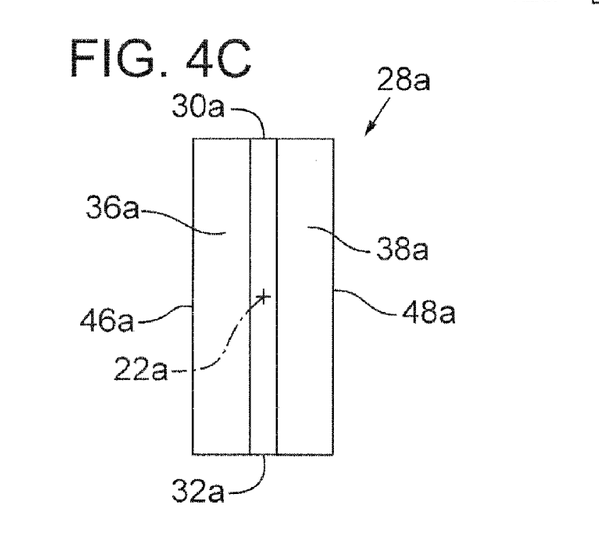

Optical element 36 and lens 38 are transparent optical elements that serve to partly confine the liquid flow in sample fluid stream 14 and to confine scattered light component 40 and direct it through light collection lens system 44 such that it is incident on photodetector element 52. In the preferred embodiment of FIG. 3, for lens 38 and optical element 36, their respective inner surfaces 68 and 70 are flat and their respective outer surfaces 48 and 46 are curved. Curved outer surfaces 46 and 48 are preferably of elliptical, aspherical, or spherical shape. FIGS. 4A, 4B, and 4C show an alternative preferred embodiment of a chamber 12a that has optically transparent windows 30a 32b through which an optical axis 22a passes. Chamber 12a includes a flow cell 28a, in which inner surfaces 68a and 70a and outer surfaces 46a and 48a are flat. In both preferred embodiments, the outer surfaces of optical elements 36 and 36a and lenses 38 and 38a interface with air.

Figure 5:
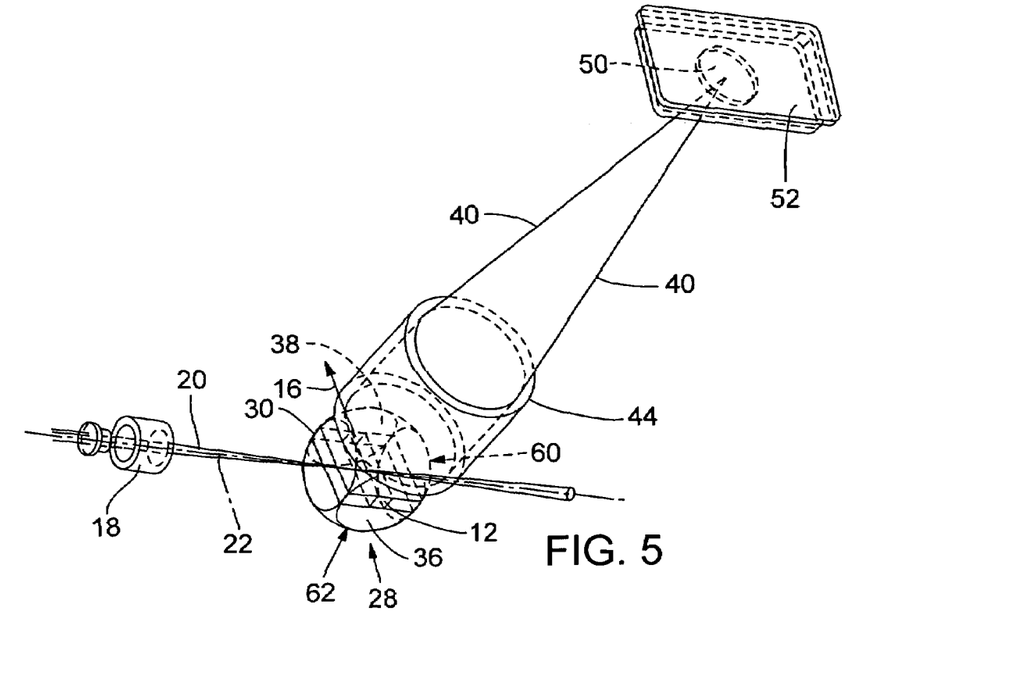
FIG. 5 is an isometric view of the unitary flow-through cell of FIGS. 3A, 3B, and 3C installed in the particle detection system of FIG. 1.

FIG. 5 is a three-dimensional isometric view of the unitary flow-through cell of FIGS. 3A, 3B, and 3C installed in the particle detection system of FIG. 1. FIGS. 3A, 3B, and 3C are illustrative of the preferred fluid-tight seals formed between optically transparent windows 30 and 32, optical element 36, and lens 38. The use of unitary flow-through cell 28 in particle detection system 10 minimizes the mechanical interference that causes scattering and absorption of light within particle detection system 10 by, for example, bonding joints. Further, mechanical centering of unitary flow-through cell 28 within the optical system (light collection lens system 44 and photodetector element 52) is more precise when using unitary flow-through cell 28 because the square edges of flow-through cell 28 facilitate its placement within particle detection system 10. The mechanical design features are described below with reference to FIGS. 8A and 8B.

The positioning of a lens along a light collection lens system axis increases the numerical aperture of the light collection lens system, thereby increasing the amount of light collected by the light collection system, the amount of light incident on the light detector element, and, as a consequence, the magnitude of the resulting pulse output signal. When the pulse output signal magnitude corresponding to a detected sample particle is increased, the pulse output threshold level that differentiates noise from valid particle detection signals may be lowered. The ability of the particle detection system of the present invention to distinguish low-amplitude pulse output signals from noise enables the system to detect smaller diameter particles than those detectable by prior art particle detection systems.

Figure 6:
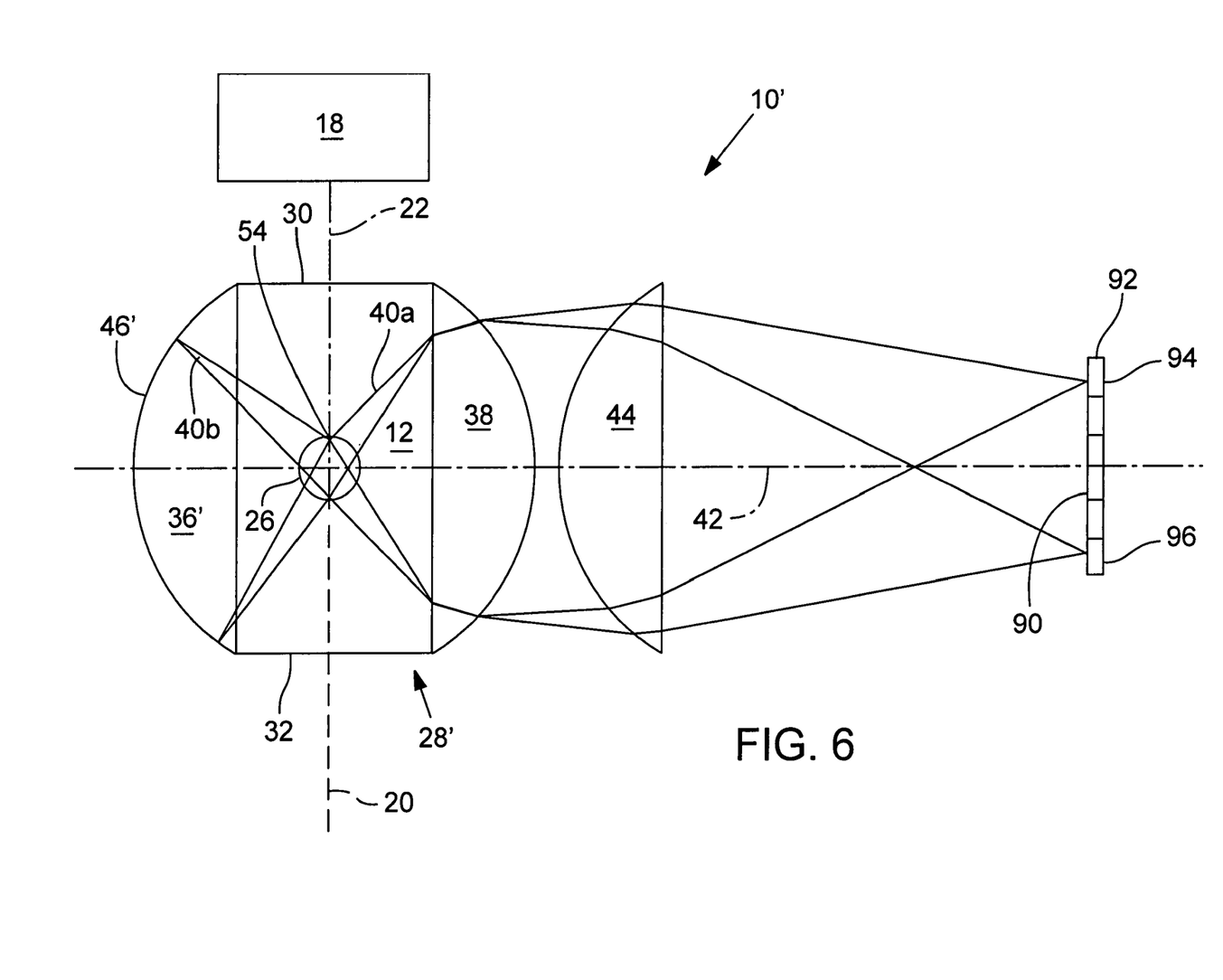
FIG. 6 is an enlarged, simplified plan view of an alternative exemplary implementation of the particle detection system of FIG. 1.
Figure 7:
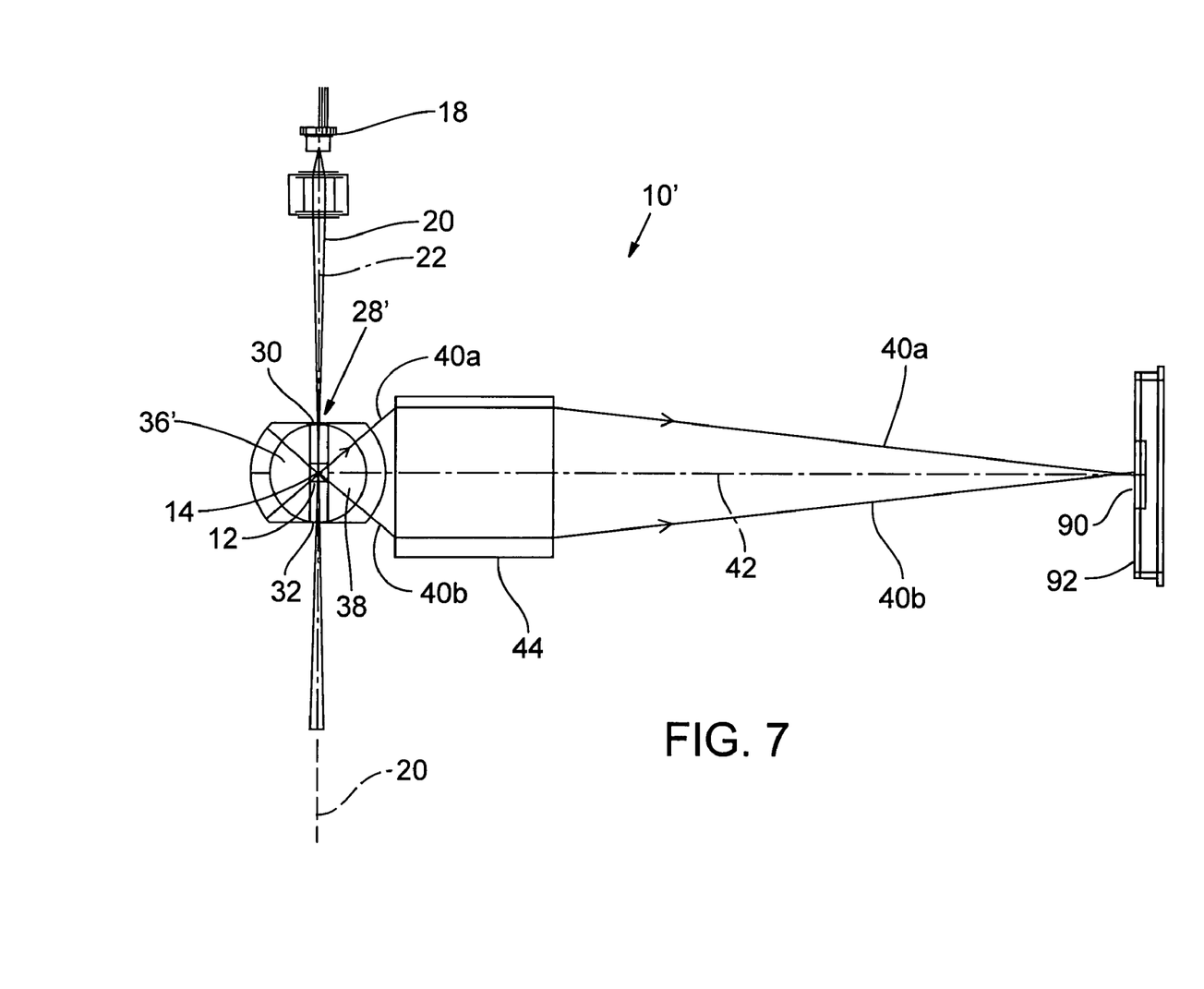
FIG. 7 is a plan view of the particle detection system of FIG. 6.

An exemplary preferred particle detection system that includes a light-reflecting optical element 36' is shown in FIGS. 6 and 7. Light-reflecting optical element 36' of flow-through cell 28' is preferably a light reflector in the form of a curved segment having an outer surface that is of spherical, elliptical, or aspherical shape. An outer surface 46' of light-reflecting optical element 36' is coated with a high-reflectance coating. Light-reflecting optical element 36' is preferably a mirror and is positioned opposite light collection lens system 44, with view volume 26 and lens 38 disposed between them. Light-reflecting optical element 36' is centered on collection system axis 42 such that the center of curvature of light-reflecting optical element 36' is aligned with the effective center of view volume 26. In a preferred implementation, light-reflecting optical element 36' has a diameter that is the same as the diameter of lens 38, which arrangement doubles the amount of scattered light collected by light collection lens system 44.

FIG. 6 is useful in the explanation of the processing of scattered light components 40a and 40b formed by the incidence of light beam 20 on particle 54. The incidence of light beam 20 on particle 54 scatters correlated light components 40a and 40b from view volume 26 in respective first and second directions. Scattered light component 40a exits view volume 26 in a direction generally toward lens 38 and light collection lens system 44, and scattered light component 40b exits view volume 26 in a direction generally away from lens 38 and toward light-reflecting optical element 36'. Scattered light component 40b is incident on light-reflecting optical component 36', which acts as a light reflector that reflects and inverts about optical axis 22 scattered light component 40b. Scattered light component 40b returns to view volume 26 in an inverted state at a location approximately the same distance from, but on the opposite side of, collection system axis 42 as that of scattered light component 40a. Both scattered light components 40a and 40b propagate in a direction along collection system axis 42 through light collection lens system 44 that converges light components 40a and 40b onto a light-receiving surface 90 of a photodetector array 92.

Photodetector array 92 is positioned, so that its light-receiving surface 90 is substantially perpendicular to, and the number of detector elements in the linear array is bisected by, collection system axis 42. Collection system axis 42 divides photodetector array 92 into two sets of detector elements, one that contains a first detector element 94 and another that contains a second detector element 96. Detector elements 94 and 96 are preferably equidistant from collection system axis 42.

Scattered light component 40a propagates through light collection lens system 44 and is focused onto detector element 94 of photodetector array 92. The inverted scattered light component 40b propagates through view volume 26 and light collection lens system 44, which focuses inverted scattered light component 40b onto detector element 96 of photodetector array 92. Detector elements 94 and 96 constitute a related pair of detector elements of photodetector array 92 such that detector element 94 is spatially related to scattered light component 40a and such that detector element 96 is spatially related to inverted scattered light component 40b. Each of detector elements 94 and 96 detects the incidence of light and generates a pulse output signal, the magnitude of which depends on the intensity of the incident scattered light component. Only those pulse output signals that are temporally and spatially coincident such that both of detector elements 94 and 96 of the pair of detector elements concurrently generate pulse output signals are processed by the signal processing system downstream of the photodetector elements. If each of the pulse output signals concurrently crosses its predetermined threshold, the signal processing system filters the pulse output signals to remove noise and amplifies the signals to generate a final pulse output signal indicating the presence and size of the sample particle. If the pulse output signal from either of detector elements 94 and 96 does not exceed the predetermined threshold, the signal is ignored by particle detection system 10' and is not further processed. If the pulse output signals from detector elements 94 and 96 are not coincident, they are ignored by particle detection system 10' and are not further processed.

Photodetector array 92 is preferably a linear array of photodiode detectors having dimensions that are proportional to the image dimensions of view volume 26. Exemplary detector arrays include an avalanche photodetector (APD) array, a photomultiplier tube (PMT) array with an array of anodes, and a photodetector (PD) array. An exemplary commercially available photodetector array is the Perkin Elmer Optoelectronics Model C30985E, with 25 detector elements each measuring 0.3 mm center-to-center. An array of photodiode detectors is used for the purpose of detecting coincidence and thereby reducing noise and false counts.

While many signal processing systems are known to those skilled in the art, exemplary preferred signal processing systems for use in connection with the particle detection system of the present invention are described in U.S. Pat. No. 6,784,990 to DeFreez et al., which is hereby incorporated by reference.

Particle detection systems implemented with an immersed optical system as described above have an increased ability to distinguish between noise and low-amplitude pulse output signals caused by small-diameter particles. Signal enhancement results from the inclusion of lens 38 in unitary flow-through cell 28. The immersion of lens 38 next to sample fluid stream 14 flowing in unitary flow-through cell 28 increases the numerical aperture of light collection lens system 44 by the index of refraction of the sample fluid medium:

$$NA = N(\sin\theta),$$

where NA is the numerical aperture, N is the index of refraction of the medium, and $\theta$ is the collection system input half-angle. For example, an exemplary prior art particle detection system constructed with a refractive lens system for collecting light scattered from particles originating from a liquid source, passing through a window, and propagating through air has a numerical aperture of 0.64. When a lens is placed next to the liquid medium (e.g., water), the numerical aperture increases by the index of refraction of the water (1.33). Thus, the numerical aperture of the particle detection system including a lens is $$NA = (0.64)(1.33) = 0.85.$$

The amount of light collected is increased by 1.9, as computed using solid angles, which is roughly the square of the NA ratio.

Increasing the numerical aperture increases the collection angle and thereby increases the amount of light collected by light collection lens system 44. An immersed reflector of the same diameter as the diameter of the opposing lens in a system such as that described with reference to FIGS. 6 and 7 doubles the amount of light collected from a particle. An increase in the amount of light collected results in an increase in the magnitude of the pulse output signal generated by a photodetector element. For the reasons stated above, increasing the pulse output signal magnitude resulting from the detection of each sample particle permits the use of a higher threshold to differentiate noise from valid particle detection signals. The threshold for a given false count rate may, therefore, be increased and the particle detection system can still maintain the desired overall false count rate, since most noise is random and of insufficient magnitude to generate a pulse output signal that has a magnitude greater than the threshold.

Figure 8A:
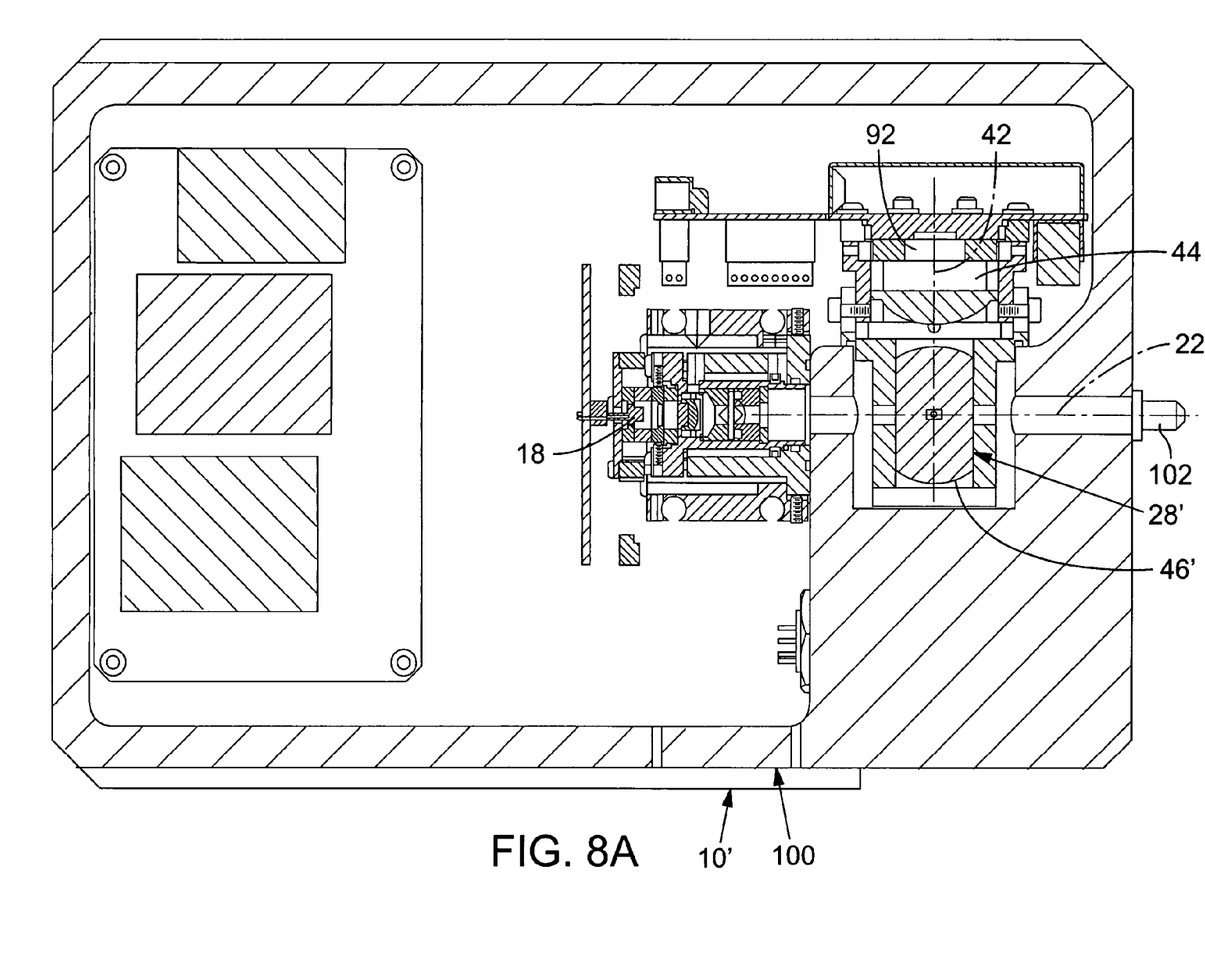
FIGS. 8A and 8B are, respectively, plan and side elevation views showing in cross-section a particle detection system housing in which the unitary flow-through cell of FIGS. 6 and 7 are installed.
Figure 8B:
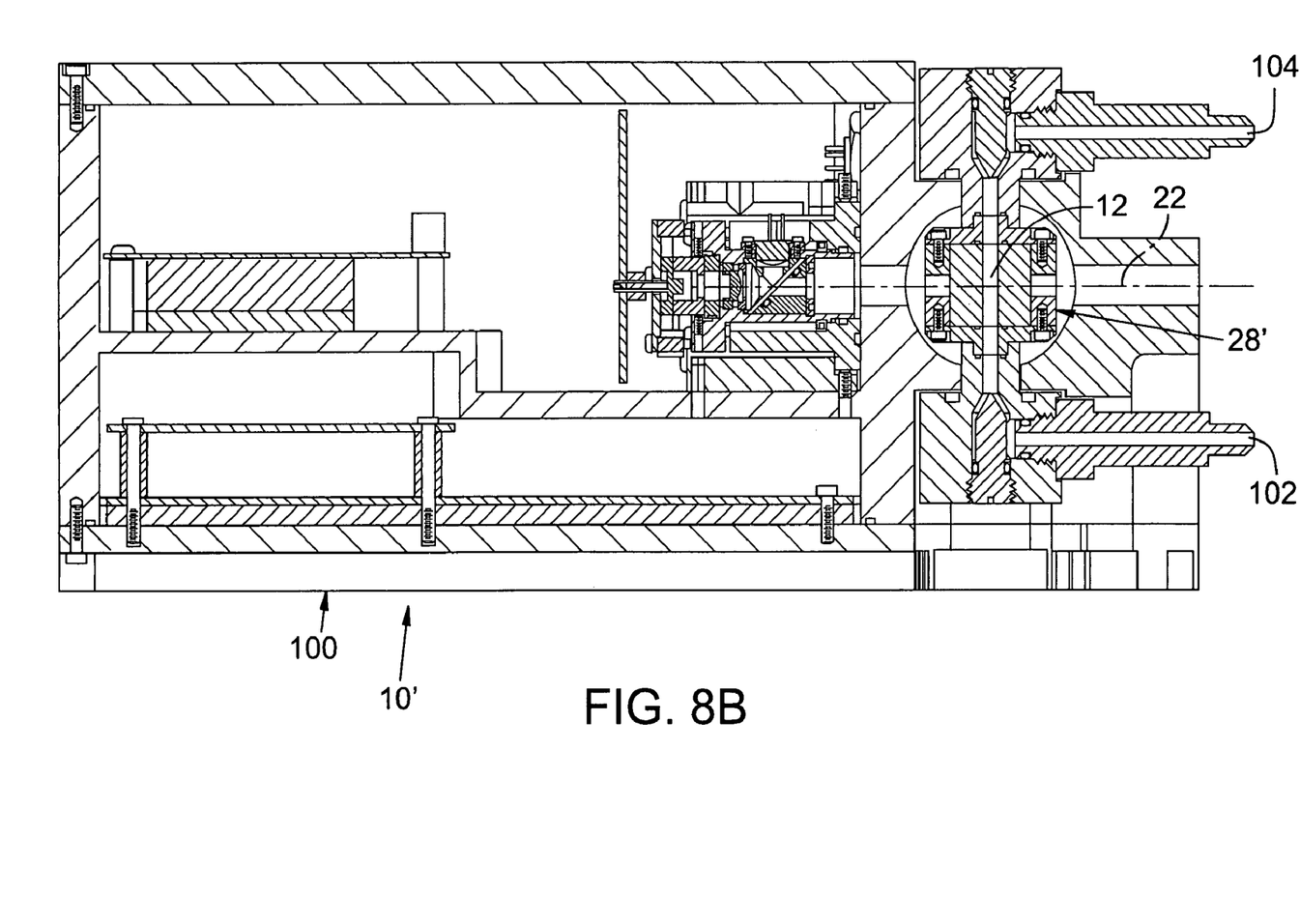

FIGS. 8A and 8B are respective plan and side elevation views showing in cross-section particle detection system 10' with flow cell 28' installed in a housing 100. FIG. 8A shows the angular offset of beam axis 22 and collection system axis 42 and exhibits the role of flat major surfaces 68 and 70 in achieving a compact fit within housing 100. FIG. 8B shows the intersection of beam axis 22 with flow chamber 12, which receives fluid flow from an inlet 102 and discharges fluid flow through an outlet 104.

It will be obvious to those having skill in the art that many changes may be made to the details of the above-described embodiments of this invention without departing from the underlying principles thereof. The scope of the present invention should, therefore, be determined only by the following claims.

The invention claimed is:

1. In a particle detection system for detecting particles entrained in a fluid stream that flows along a flow axis, the particle detection system having a view volume in which a light beam propagating along a light propagation path transversely intersects the fluid stream such that entrained particles upon which the light beam is incident cause portions of the light beam to scatter from the view volume as scattered light components, at least some of the scattered light components propagating through a light collection lens system that has a light collection lens system axis and being incident on a light detector that produces a signal representing the intensity of the scattered light components propagating through the collection lens system and incident on the light detector, the improvement comprising:

- a foxy-though cell including first and second body sections coupled to form a unitary article, the first and second body sections associated with respective first and second optical elements;
- each of the first and second body sections having opposed interior surface portions configured to form opposed walls of a flow channel through which the fluid stream flows;
- a pair of spacers positioned between and coupled to the first and second body sections, the spacers spaced apart from each other to define the opposed interior surface portions that form the opposed walls of the flow channel; and
- the unitary flow-through cell sized for insertion into the particle detection system in an orientation that positions the first and second optical elements along the light collection lens system axis.

2. The particle detection system of claim 1, in which the pair of spacers is formed of optically transparent material to function as ingress and egress windows of the view volume for the light beam.

3. The particle detection system of claim 2, in which the light beam has a beam width and the light beam egress window has a window width, the beam width and the window width being substantially the same to illuminate the entire flow channel.

4. The particle detection system of claim 2, in which the light beam has a beam width and the light beam egress window has a window width, the beam width being focused to a size that is smaller than the window width to enable higher intensity light detection of smaller particles entrained in the fluid stream.

5. The particle detection system of claim 1, in which the first and second body sections and the pair of spacers are fused into an integral structure, the pair of spacers defining surface interfaces between the spacers and the first and second body sections without bonding material present.

6. The particle detection system of claim 1, in which the second body section is positioned between the view volume and the light collection lens system when the unitary flow-through cell is inserted into the particle detection system.

7. The particle detection system of claim 6, in which the first optical element is selected from a group consisting essentially of a transparent optical element, a lens, and a mirror.

8. The particle detection system of claim 6, in which the second optical element is a lens.

9. In a particle detection system for detecting particles entrained in a fluid stream that flows along a flow axis, the particle detection system having a view volume in which a light beam propagating along a light propagation path transversely intersects the fluid stream such that entrained particles upon which the light beam is incident cause portions of the light beam to scatter from the view volume as scattered light components, at least some of the scattered light components propagating through a light collection lens system that has a light collection lens system axis and being incident on a light detector that produces a signal representing the intensity of the scattered light components propagating through the collection lens system and incident on the light detector, the improvement comprising:

- a flow-though cell including first and second body sections coupled to form a unitary article, the first and second body sections associated with respective first and second optical elements one of which being an integral part of its associated body section;
- each of the first and second body sections having interior surface portions configured to form opposed walls of a flow channel through which the fluid stream flows; and
- a pair of spacers positioned between and coupled to the first and second body sections, the spacers spaced apart from each other to define the opposed interior surface portions that form the opposed walls of the flow channel.

10. The particle detection system of claim 9, in which the one of the first and second optical elements being an integral part is a lens.

11. The particle detection system of claim 9, in which the one of the first and second optical elements being an integral part includes one of the interior surface portions configured to form opposed walls of a flow channel.

12. The particle detection system of claim 9, in which the pair of spacers is formed of optically transparent material to function as ingress and egress windows of the view volume for the light beam.

13. The particle detection system of claim 12, in which the light beam has a beam width and the light beam egress window has a window width, the beam width and the window width being substantially the same to illuminate the entire flow channel.

14. The particle detection system of claim 12, in which the light beam has a beam width and the light beam egress window has a window width, the beam width being focused to a size that is smaller than the window width to enable higher intensity light detection of smaller particles entrained in the fluid stream.

15. The particle detection system of claim 9, in which the first and second body sections and the pair of spacers arc fused into an integral structure, the pair of spacers defining surface interfaces between the spacers and the first and second body sections without bonding material present.

16. The particle detection system of claim 9, in which the second body section is positioned between the view volume and the light collection lens system when the flow-through cell is inserted into the particle detection system.

17. The particle detection system of claim 9, in which the first optical element is selected from a group consisting essentially of a transparent optical element, a lens, and a mirror.

18. The particle detection system of claim 9, in which the second optical element is a lens.

* * * * *